United States Patent [19]
Baker et al.

[11] Patent Number: 6,096,766
[45] Date of Patent: Aug. 1, 2000

[54] 3-BENZYLAMINOPIPERIDINES AS TACHYKININ RECEPTOR ANTAGONISTS

[75] Inventors: Raymond Baker, Uley; Jason Matthew Elliott, Knockholt; Christopher John Swain, Duxford, all of United Kingdom

[73] Assignee: Merck Sharp & Dohme Ltd., Hoddesdon, United Kingdom

[21] Appl. No.: 09/091,086

[22] PCT Filed: Dec. 6, 1996

[86] PCT No.: PCT/GB96/02998

§ 371 Date: Jun. 9, 1998

§ 102(e) Date: Jun. 9, 1998

[87] PCT Pub. No.: WO97/21702

PCT Pub. Date: Jun. 19, 1997

[30] Foreign Application Priority Data

Dec. 11, 1995 [GB] United Kingdom ............. 9525296

[51] Int. Cl.[7] .............. A61K 31/445; C07D 401/12; C07D 403/12
[52] U.S. Cl. ............. 514/326; 514/381; 514/383; 514/394; 514/406; 514/422; 546/210; 546/211; 548/254; 548/255; 548/287.2; 548/314.7; 548/384.1; 548/557
[58] Field of Search ............. 546/210, 211; 548/254, 255, 287.2, 314.7, 384.1, 557; 814/326, 381, 383, 394, 406, 422

[56] References Cited

U.S. PATENT DOCUMENTS

| | | | |
|---|---|---|---|
| 5,232,929 | 8/1993 | Desai | 514/314 |
| 5,703,240 | 12/1997 | Armour | 514/210 |
| 5,728,716 | 3/1998 | MacCoss et al. | 514/326 |

FOREIGN PATENT DOCUMENTS

| | | |
|---|---|---|
| WO 94/04496 | 3/1994 | WIPO . |
| WO 95/06645 | 3/1995 | WIPO . |
| WO 95/08549 | 3/1995 | WIPO . |

OTHER PUBLICATIONS

Ward et al. "Discovery of an orally bioavailable NK1 antagonist . . . " J. Med. chem. v.38, 4985–4992, 1995.

*Primary Examiner*—Ceila Chang
*Attorney, Agent, or Firm*—J. Eric Thies; David L. Rose

[57] ABSTRACT

The present invention relates to certain 3-benzylaminopiperidines which are tachykinin receptor antagonists and are useful in the treatment or prevention of pain, inflammation, migraine, emesis and postherpetic neuralgia.

17 Claims, No Drawings

3-BENZYLAMINOPIPERIDINES AS TACHYKININ RECEPTOR ANTAGONISTS

This application is a 371 of PC7/GB96/02998 filed Dec. 6, 1996.

This invention relates to a class of azacyclic compounds, which are useful as tachykinin antagonists. More particularly, the compounds of the invention comprise an azacyclic ring system substituted by an aralkylamino moiety.

The tachykinins are a group of naturally occurring peptides found widely distributed throughout mammalian tissues, both within the central nervous system and in peripheral nervous and circulatory systems.

The tachykinins are distinguished by a conserved carboxyl-terminal sequence:

Phe-X-Gly-Leu-Met-$NH_2$

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthmalbronchial hyperreactivity and other respiratory diseases including allergic rhinitis, inflammatory diseases of the gut including ulcerative colitis and Crohn's disease. ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in "*Trends in Cluster Headache*" Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, Nov. 11, 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster *C.I.N.P. XVIIIth Congress*, Jun. 28th–Jul. 2nd 1992], and in disorders of bladder function such as bladder detrusor hyper-reflexia (*Lancet*, May 16th 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

International Patent Specification no. WO 95/08549 discloses piperidine derivatives as tachykinin receptor antagonists of the general formula

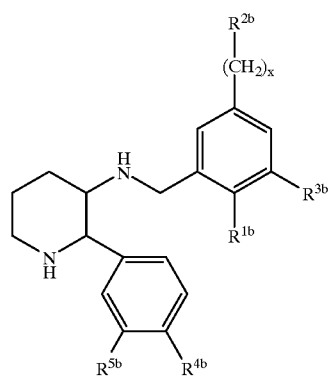

wherein $R^{1b}$ is $C_{1-4}$alkoxy;

$R^{2b}$ is optionally substituted tetrazolyl;

$R^{3b}$ is hydrogen or halogen;

$R^{4b}$ and $R^{5b}$ hydrogen, halogen, $C_{1-4}$alkyl, $C_{1-4}$alkoxy or $CF_3$; and x is zero or 1.

The present invention provides a further class of non-peptides which are antagonists of tachykinins, especially of substance P.

Thus, the present invention provides compounds of formula (I), and pharmaceutically acceptable salts and prodrugs thereof:

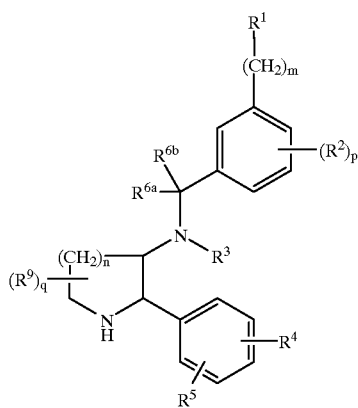

(I)

wherein
$R^1$ represents a 5- or 6-membered aromatic heterocyclic group containing 1, 2, 3 or 4 heteroatoms selected from nitrogen, oxygen and sulphur, which is optionally substituted by one or two substituents, selected from $C_{1-4}$alkyl, $C_{3-7}$cycloalkyl, $C_{3-7}$cycloalkyl$C_{1-4}$alkyl, $SR^x$, $SOR^x$, $SO_2R^x$, phenyl, $NR^aR^b$, $NR^aCOR^x$, $CH_2COCF_3$ and $CF_3$, where $R^a$ and $R^b$ are independently hydrogen or $C_{1-4}$alkyl and $R^x$ is $C_{1-4}$alkyl;

$R^2$ represents halogen, $C_{1-6}$alkyl, $C_{1-6}$alkoxy, $CF_3$, $OCF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^3$ represents hydrogen or $C_{1-6}$alkyl;

$R^4$ represents hydrogen, halogen, $C_{1-6}$alkyl, $C_{1-6}$alkoxy, hydroxy, $CF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^5$ represents hydrogen, halogen, $C_{1-6}$alkyl, $C_{1-6}$alkoxy substituted by $C_{1-4}$alkoxy or $CF_3$;

$R^{6a}$ represents hydrogen or $C_{1-6}$alkyl;

$R^{6b}$ represents $C_{1-6}$alkyl optionally substituted by a hydroxy group or the group —$CO_2R^c$, where $R^c$ represents $C_{1-6}$alkyl;

$R^9$ represents halogen, $C_{1-6}$alkyl, oxo, $CO_2R^a$ or $CONR^aR^b$;

m is zero or 1;
n is 1 or 2;
p is zero, 1 or 2; and
q is zero, 1 or 2.

As used herein, the definition of each expression, when it occurs more than once in any structure, is intended to be independent of its definition elsewhere in the same structure.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

When used herein the term halogen means fluorine, chlorine, bromine and iodine. The most apt halogens are fluorine and chlorine of which fluorine is preferred.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. In particular, the relative orientation of the 2- and 3- substituents on the azacyclic ring may give rise to cis and trans diastereoisomers, of which the cis stereochemistry is preferred. It is to be understood that all such isomers and mixtures thereof are encompassed within the scope of the present invention.

Certain particularly apt compounds of the present invention include those wherein $R^1$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each of which heteroaryl groups being optionally substituted as previously defined.

Preferred compounds of the present invention are those wherein $R^1$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each of which heteroaryl groups being optionally substituted as previously defined.

Certain particularly apt compounds of the present invention include those wherein $R^1$ is a 5-membered aromatic heterocyclic group. Preferred compounds are those wherein $R^1$ is a 5-membered aromatic heterocyclic group containing 1, 2, 3 or 4 nitrogen atoms, for instance,

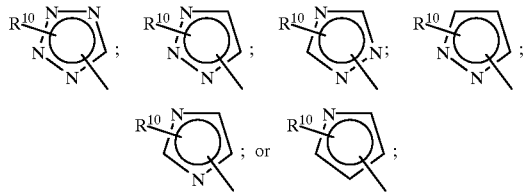

where $R^{10}$ is hydrogen, $C_{1-4}$alkyl, $C_{3-7}$cycloalkyl, $C_{3-7}$cycloalkyl$C_{1-4}$alkyl, $SR^x$, $SOR^x$, $SO_2R^x$, phenyl, $NR^aR^b$, $NR^aCOR^x$, $CH_2COCF_3$ or $CF_3$, where $R^a$ and $R^b$ are independently hydrogen or $C_{1-4}$alkyl, and $R^x$ is $C_{1-4}$alkyl.

Particularly preferred compounds of the present invention are those wherein $R^1$ is a group selected from

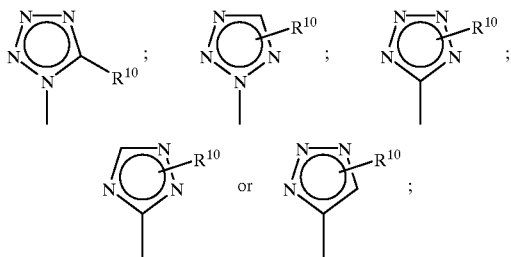

where $R^{10}$ is as previously defined.

An especially preferred class of compound of formula (I) is that wherein $R^1$ is the group

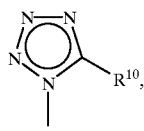

wherein $R^{10}$ is as previously defined.

$R^{10}$ is preferably hydrogen, $C_{1-4}$alkyl (especially methyl), amino, $C_{1-4}$alkylamino (especially methylamino), di($C_{1-4}$alkyl)amino (especially dimethylamino or diethylamino), $NC(O)C_{1-4}$alkyl (especially NC(O)methyl), $CH_2C(O)CF_3$ or $CF_3$.

Most aptly $R^2$ is $C_{1-4}$alkyl, $C_{1-4}$alkoxy, halogen, $CF_3$ or $OCF_3$.

Favourably $R^2$ is $C_{1-4}$alkoxy, halogen, $CF_3$ or $OCF_3$.

More preferably $R^2$ is methoxy, ethoxy, propoxy, isopropoxy, fluorine, chlorine, $CF_3$ or $OCF_3$.

Most preferably $R^2$ is in the meta- or para-position with respect to the group $R^1$—$(CH_2)_m$—.

Most preferably $R^2$ is methoxy.

Preferably $R^3$ is hydrogen or $C_{1-4}$alkyl.

Most preferably, $R^3$ is hydrogen or methyl.

Most aptly $R^4$ is hydrogen.

Most aptly $R^5$ is hydrogen, fluorine, chlorine or $CF_3$.

Preferably $R^4$ is hydrogen and $R^5$ is hydrogen or 4-fluoro.

Suitable values for $R^{6a}$ include hydrogen, methyl and ethyl.

Preferably $R^{6a}$ is hydrogen or methyl, more preferably hydrogen.

Preferably $R^{6b}$ is $C_{1-4}$alkyl optionally substituted by a hydroxy group, such as methyl, ethyl, $CH_2OH$, $CH_2CH_2OH$, $CH(OH)CH_3$ or $C(OH)(CH_3)_2$, or the group —$CO_2R^c$ where $R^c$ is $C_{1-4}$alkyl such as $C(O)OCH_3$ or $C(O)OCH_2CH_3$.

More preferably, $R^{6b}$ is methyl or $CH_2OH$.

When present, $R^9$ is preferably methyl. For the avoidance of doubt, $R^9$ is attached to any available carbon atom on the azacyclic ring.

Preferably m is zero.

Preferably n is 2.

Preferably p is zero or 1.

Preferably q is zero.

A particular sub-class of compounds according to the present invention is represented by compounds of formula (Ia), and pharmaceutically acceptable salts and prodrugs thereof:

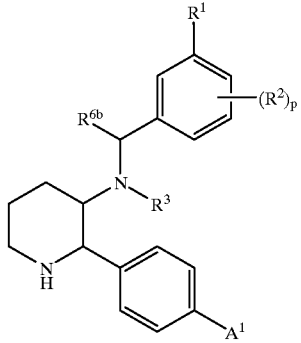

wherein
$R^1$, $R^2$, $R^3$, $R^{6b}$ and p are as defined for formula (I) above; and $A^1$ is fluorine or hydrogen.

Specific compounds within the scope of the present invention include:

(±)-2,3-cis-N-{1-[2-methoxy-5-(1H-tetrazol-1-yl)phenyl]ethyl}-2-phenylpiperidin-3-amine;

(±)-2,3-cis-2-[(2-phenylpiperidin-3-yl)amino]-2-[2-methoxy-5-(1H-tetrazol-1-yl)phenyl]ethanol;

and pharmaceutically acceptable salts and prodrugs thereof.

Further preferred compounds within the scope of the present invention are described in the Examples described herein.

In a further aspect of the present invention, the compounds of formula (I) will preferably be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

Thus, for example, certain preferred prodrugs may not be antagonists of tachykinin, particularly substance P, activity to any significant extent (or not at all). Such compounds, however, are still advantageous in treating the various conditions described herein, especially where an injectable formulation is preferred.

The advantages of a prodrug may lie in its physical properties, such as enhanced water solubility for parenteral administration compared with the parent drug, or it may enhance absorption from the digestive tract, or it may enhance drug stability for long-term storage. Ideally a prodrug will improve the overall efficacy of a parent drug, for example, through the reduction of toxicity and unwanted effects of drugs by controlling their absorption, blood levels, metabolism, distribution and cellular uptake.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and(Ia) will have the 2- and 3- substituent cis and the preferred stereochemistry at the 2-position is 2-(S)- whilst the preferred stereochemistry of the 3-position is 3-(S).

Thus for example as shown in formula (Ib)

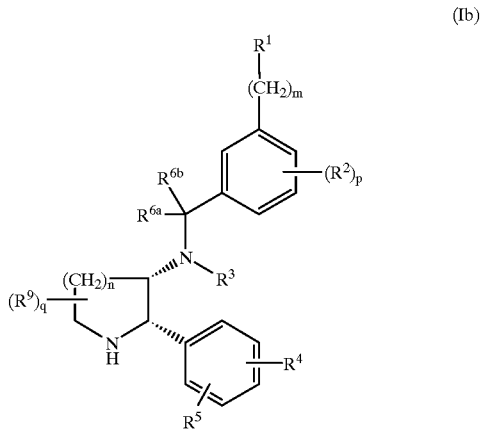

(Ib)

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include anionic agents such as sodium bis-(2-ethylhexyl)sulfosuccinate (docusate sodium), cationic agents, such as alkyltrimethylammonium bromides, (e.g. cetyltrimethylammonium bromide (cetrimide)), and in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or sovbean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives. sedatives, hypnotics, and anxiolytics, which substance-related disorders include dependence and abuse, intoxication, withdrawal, intoxication delerium, withdrawal delerium, persisting dementia. psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica: ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm: inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vombiting: Recent Research and Clinical Advainces*, Eds. J. Kucharczyk et al, CRC Press Inc. Boca Raton. Fla., USA (1991) pages 177–203, especially page 188. Commonly used chemotherapeutic agents include cisplatin, dacarbazine (DTIC), dactinomycin, mechlorethamine (nitrogen mustard). streptozocin. cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABA$_B$ receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126.375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general. the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250. R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270, 324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, specially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antuinflammatory agent such as a bradvkinin receptor antagonist.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and $5\text{-HT}_{1A}$ agonists or antagonists, especially $5\text{-HT}_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable $5\text{-HT}_{1A}$ receptor agonists or antagonists include, in particular, the $5\text{-HT}_{1A}$ receptor partial agonists buspirone, flesinoxan, gepirone and ipsaperone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation. a suitable dosage level is about 0.001 to 10 mg/kg per day, preferably about 0.005 to 5 mg/kg per day, and especially 0.01 to 2 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The compounds according to the present invention may be prepared by a process (A) which comprises reacting a compound of formula (II) with a compound of formula (III):

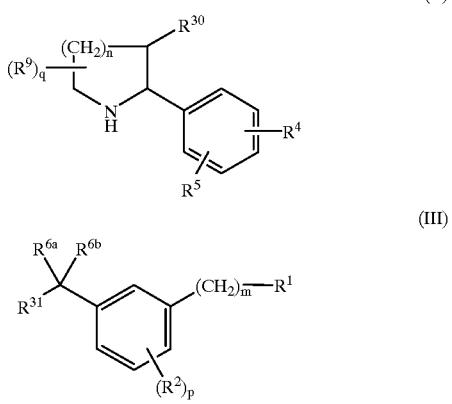

wherein $R^1$, $R^2$, $R^4$, $R^5$, $R^{6a}$, $R^{6b}$, $R^9$ m, n, p and q are as defined for formula (I), except that any reactive moiety is protected by a suitable protecting group; and one of $R^{30}$ and $R^{31}$ represents a leaving group and the other of $R^{30}$ and $R^{31}$ represents $NHR^3$, where $R^3$ is as defined for formula (I); in the presence of a base, followed by deprotection, if required.

Suitably $R^{30}$ represents $NHR^3$ and $R^{31}$ represents a leaving group.

Suitable leaving groups include halogen atoms, e.g. chlorine, bromine or iodine, or sulphonate derivatives such as tosylate, mesylate or triflate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, sodium hydride is used.

According to another process (B), compounds of formula (I) wherein $R^{6a}$ is hydrogen, may be prepared by the reductive amination of a compound of formula (II) in which $R^{30}$ is the group $NHR^3$, with a compound of formula (IV), in the presence of a reducing agent:

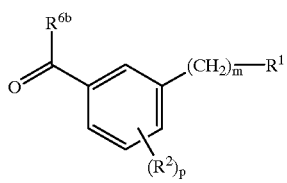

Suitable reducing agents for use in this reaction include, for example, sodium cyanoborohydride or sodium triacetoxyborohydride, or catalytic hydrogenation. The reaction is conveniently effected in a suitable solvent such as acetic acid or methanol at a temperature between 0° C. and 50° C., conveniently at about room temperature.

According to another general process (C), compounds of formula (I) wherein m is zero and $R^1$ is a tetrazol-1-yl group substituted by a 5-amino moiety may be prepared by reaction of intermediates of formula (V)

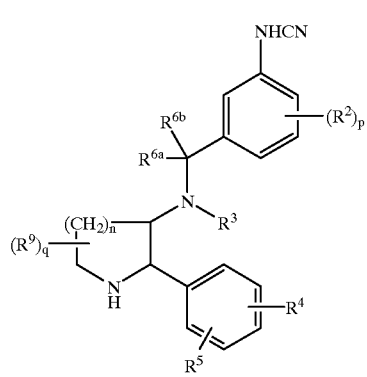

with ammonium chloride and sodium azide at elevated temperature, conveniently in a solvent such as dimethylformamide.

According to another general process (D), compounds of formula (I) may be prepared by a coupling reaction between a compound of formula (I) and (VII)

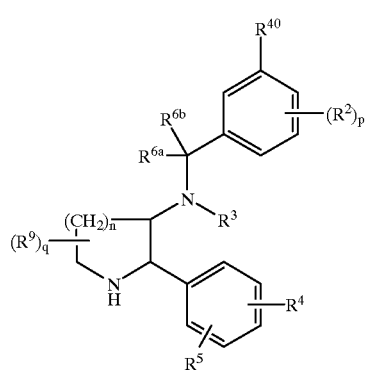

wherein one of $R^{40}$ and $R^{41}$ is $B(OH)_2$ or $Sn(alkyl)_3$ or a derivative thereof, and the other is a leaving group such as a halogen atom e.g. bromine or iodine, or $-OSO_2CF_3$.

Where one of $R^{40}$ and $R^{41}$ is $B(OH)_2$, the reaction is conveniently effected in the presence of a palladium (0) catalyst such as tetrakis(triphenylphosphine)palladium (0) in a suitable solvent such as an ether, for example, dimethoxyethane at an elevated temperature. Where one of $R^{40}$ and $R^{41}$ is $Sn(alkyl)_3$, the reaction is conveniently effected in the presence of palladium (II) catalyst such as bis(triphenylphosphine) palladium (II) chloride, in a suitable solvent such as an aromatic hydrocarbon, for example, toluene, at an elevated temperature.

According to another general process (E), compounds of formula (I) may be prepared by reduction of a compound of formula (VIII)

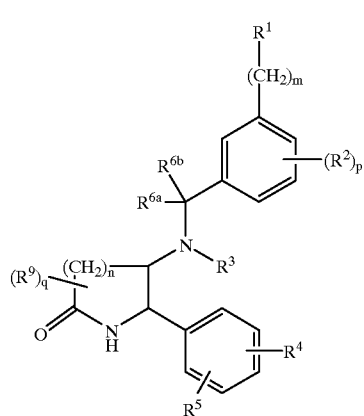

(VIII)

(with the proviso that $R^9$ is not oxo). Suitable reducing agents will be readily apparent to one skilled in the art and include, for example, borane or metallic hydrides, such as lithium aluminium hydride or sodium borohydride. Borane is preferred.

Further details of suitable procedures will be found in the accompanying Examples.

Compounds of formula (VIII) may be prepared by reductive amination of a compound of formula (IX)

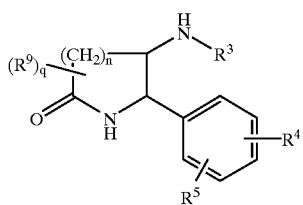

(IX)

wherein any reactive moiety is protected by a suitable protecting group using, for example, sodium cyanoborohydride or sodium triacetoxyborohydride and a compound of the formula (III) in which $R^{31}$ is a leaving group such as a halogen atom, for example, a bromine atom. The reaction is effected in the presence of a base, for example, potassium carbonate and in a suitable solvent such as dimethylformamide.

It will be appreciated that the product of the reductive amination method described herein will be a mixture of stereoisomers at the position of the group $R^{6a}$. For the subsequent preparation of a specific isomer of a compound of formula (I) wherein $R^{6a}$ is hydrogen and $R^{6b}$ is, for example, $C_{1-6}$alkyl, the mixture of stereoisomers may be resolved by conventional methods, for example, by column chromatography.

Methods for the preparation of intermediates of formula (IX) and formula (II) when $R^{30}$ is $NHR^3$ are described, for example, in European Patent Specification No. 0 436 334.

Where they are not commercially available, the intermediates of formulae (III), (IV) and (VII) above may be prepared by procedures which will be readily apparent to one skilled in the art, for instance, using methodology such as that described in International Patent Specification No. WO 95/08549, published Mar. 30th 1995.

Intermediates of formula (VI) may be prepared by method analogous to those described herein.

Where the above-described processes for the preparation of the compounds according to the invention give rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, compounds which contain a hydroxy group may be resolved into their component enantiomers by standard techniques, such as the formation of diastereomeric esters or amides, followed by chromatographic separation or separation by fractional crystallization and removal of the chiral auxiliary. Where they are intermediates, diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

Tachykinin antagonist activity for compounds of the present invention may be demonstrated by the methods set out at pages 36 to 39 of International Patent Specification No. WO 93/01165.

The compounds of this invention may be formulated as specifically illustrated at pages 35 to 36 of International Patent Specification No. WO 93/01165.

The following Examples illustrate the preparation of compounds according to the invention.

EXAMPLE 1

(±)-2,3-cis-N-{1-[2-Methoxy-5-(1H-tetrazol-1-yl)phenyl]ethyl}-2-phenylpiperidin-3-amine dihydrochloride (i) N-(3-Acetyl-4-methoxyphenyl)acetamide Methyl iodide (3.42 ml, 7.81 g, 55 mmol) was added to a stirred mixture of N-(3-acetyl-4-hydroxyphenyl)acetamide (*J.Org.Chem.* 1995, 60, 4324–4330) (9.65 g, 50 mmol) and potassium carbonate (13.82 g, 100 mmol) in dimethylformamide (50 ml). The mixture was stirred at room temperature for 72 hours, then the solvent was evaporated under reduced pressure. Water (100 ml) was added and the mixture was extracted with ethyl acetate (6×100 ml). The combined organic fractions were dried (MgSO$_4$) and evaporated under reduced pressure to give N-(3-acetyl-4-methoxyphenyl)acetamide as a tan solid (10.34 g, 100%), $^1$H NMR (d$_6$-DMSO) δ 9.91 (1H, br. s), 7.76 (2H, m), 7.12 (1H, d, J=9.6 Hz), 3.86 (3H, s), 2.52 (3H, s), and 2.01 (3H, s). m/e (CI$^+$) 208 (MH$^+$).

(ii) 1-(5-Amino-2-methoxyphenyl)ethanone

Hydrochloric acid (6M, 50 ml) was added to a mixture of N-(3-acetyl-4-methoxyphenyl)acetamide (10.34 g, 50 mmol) and ethanol (150 ml) and the mixture was stirred under reflux for 8 hours. The mixture was cooled and the solvent was evaporated under reduced pressure. Water (100 ml) was added and the pH was adjusted to 10.0 with saturated aqueous potassium carbonate. The mixture was extracted with dichloromethane (3×100 ml) and the combined organic fractions were dried (MgSO$_4$) and evaporated under reduced pressure to give 1-(5-amino-2-methoxyphenyl)ethanone as a dark oil (8.16 g, 99%), $^1$H NMR (CDCl$_3$) δ 7.09 (1H, d, J=2.8 Hz), 6.82 (2H, m), 3.84 (3H, s), and 3.34 (2H, br. s), 2.59 (3H, s). m/e (CI$^+$) 166 (MH$^+$).

(iii) 1-[2-Methoxy-5-(1H-tetrazol-1-yl)phenyl]ethanone

Triethyl orthoformate (28.79 ml, 25.65 g, 173 mmol) was added to a stirred, heated (80° C.) solution of 1-(5-amino-2-methoxyphenyl)ethanone (8.16 g, 49 mmol) in acetic acid (80 ml) and the mixture was stirred at 75° C. for 1 hour. Sodium azide (9.64 g, 148 mmol) was added in portions over 90 minutes, then the mixture was stirred at 75° C. for 4 hours. The mixture was cooled to room temperature and the solvent was evaporated under reduced pressure. Hydrochloric acid (1M, 100 ml) was added and the mixture was stirred at room temperature 1 hour. The solid was collected, flushed with toluene (100 ml) and dried in vacuo at room temperature. The residue was recrystallized from ethanol (700 ml) to give 1-[2-methoxy-5-(1H-tetrazol-1-yl)phenyl]ethanone as tan coloured needles (7.88 g, 73%), $^1$H NMR (d$_6$-DMSO) δ 10.06 (1H, s), 8.06 (2H, m), 7.46 (1H, d, J=7.8 Hz), 3.99 (3H, s), and 2.60 (3H, s). m/e (CI$^+$) 219 (MH$^+$)

(iv) (±)-2,3-cis-N-{1-[2-Methoxy-5-(1H-tetrazol-1-yl)phenyl]ethyl}-2-phenylpiperidin-3-amine Titanium tetrachloride (1.0 M solution in dichloromethane, 0.3 ml, 0.3 mmol) was added dropwise to a stirred, cooled (0° C.) mixture of (2R3R, 2S3S)-cis-2-phenylpiperidin-3-amine (106 mg, 0.6 mmol), 1-[2-methoxy-5-(1H-tetrazol-1-yl)phenyl]ethanone (131 mg, 0.6 mmol) and triethylamine (0.25 ml, 182 mg, 1.8 mmol) in dichloromethane (10 ml). The mixture was stirred at room temperature for 1 hour, cooled in ice and sodium cyanoborohydride (113 mg, 1.8 mmol) in methanol (2 ml) was added. The mixture was stirred at room temperature for 30 minutes, then hydrochloric acid (1M, 5 ml) was added. The mixture was stirred at room temperature for 1 hour, ethyl acetate (40 ml) was added and the mixture was extracted with hydrochloric acid (1M, 3×20 ml). The combined aqueous fractions were washed with ethyl acetate (2×20 ml), adjusted to pH 9.0 with saturated aqueous potassium carbonate and extracted with ethyl acetate (3×20 ml). The combined organic fractions were washed with saturated sodium hydrogen carbonate (20 ml), dried (MgSO$_4$) and evaporated under reduced pressure to give crude (±)-2,3-cis-N-{1-[2-methoxy-5-(1H-tetrazol-1-yl)phenyl]ethyl}-2-phenylpiperidin-3-amine as a colourless foam (134 mg).

(v) (±)-2,3-cis-N-{1-[2-Methoxy-5-(1H-tetrazol-1-yl)phenyl]ethyl}-1-tert-butoxycarbonyl-2-phenylpiperidin-3-amine Di-tert-butyldicarbonate (218 mg, 1 mmol) in dichloromethane (2 ml) was added to a stirred, cooled (0° C.) solution of crude (±)-2,3-cis-N-{1-[2-methoxy-5- (1H-tetrazol-1-yl)phenyl]ethyl}-2-phenylpiperidin-3-amine (319 mg) in dichloromethane (5 ml) and the mixture was stirred at room temperature for 16 hours. Saturated aqueous sodium hydrogen carbonate (20 ml) and water (10 ml) were added and the mixture was extracted with dichloromethane (3×20 ml). The combined organic fractions were dried (MgSO$_4$) and evaporated under reduced pressure. The residue was purified by flash column chromatography on silica gel, eluting with ethyl acetate/hexane (40:60 increasing to 70:30) to give (±)-2,3-cis-N-{1-[2-methoxy-5- (1H-tetrazol-1-yl)phenyl]ethyl}1-tert-butoxycarbonyl-2-phenylpiperidin-3-amine as a colourless foam (206 mg, 29% from [2R3R, 2S3S]-cis-2-phenylpiperidin-3-amine), $^1$H NMR (CDCl$_3$) δ 9.00, 8.67 (total 1H, each s), 7.77–6.94 (8H, m), 5.47, 5.16 (total 1H, each br. m), 4.39 (1H, m), 3.93, 3.85 (total 3H, each s), 3.90 (1H, m), 3.04–2.80 (2H, m), and 1.84–1.16 (17H, m).

(vi) (±)-2,3-cis-N-{1-[2-Methoxy-5-(1H-tetrazol-1-yl)phenyl]ethyl}-2-phenylpiperidin-3-amine dihydrochloride Ethanolic hydrogen chloride (5M, 4 ml) was added to a stirred, cooled (0° C.) solution of (±)-2,3-cis-N-{1-[2-methoxy-5-(1H-tetrazol-1-yl)phenyl]ethyl}-1-tert-butoxycarbonyl-2-phenylpiperidin-3-amine (206 mg, 0.43 mmol) in ethanol (2 ml) and the mixture was stirred at room temperature for 90 minutes. The solid was collected and dried in vacuo at 60° C. to give (±)-2,3-cis-N-{1-[2-methoxy-5-(1H-tetrazol-1-yl)phenyl]ethyl}(2-phenylpiperidin-3-yl)amine dihydrochloride as a colourless solid (176 mg, 90%), mp 241–243° C. $^1$H NMR (d$_6$-DMSO)δ 10.60–9.45 (4H, m), 7.92–7.15 (8H, m). 4.77, 4.12 (total 1H, each br. s), 3.74, 3.59 (total 3H, each s), 3.71–3.10 (5H, m). and 2.38–1.34 (7H, m). m/e (CI) 379 (MH$^+$).

Analysis: C$_{21}$H$_{26}$N$_6$O.2HCl.0.3H$_2$O requires: C, 55.22; H, 6.18; N, 18.07: Found: C, 55.22; H, 6.31; N, 18.40%. HPLC analysis (210 nm) showed this to consist of a 66:34 mixture of diastereoisomers.

EXAMPLE 2

(±)-2,3-cis-Methyl 2-[(2-phenylpiperidin-3-yl) amino]-2-[2-methoxy-5-(1H-tetrazol-1-yl)phenyl] ethanoate dihydrochloride (i) 2-[2-Methoxy-5-(1H-tetrazol-1-yl)phenyl]-2-oxoethanoic acid Selenium dioxide (2.50 g, 22.5 mmol) was added to a suspension of 1-[2-methoxy-5-(1H-tetrazol-1-yl)phenyl] ethanone (3.27 g, 15 mmol; from step (iii) of Example 1) in pyridine (25 ml) and the mixture was stirred at 100° C. for 3 hours. The mixture was filtered, cooled and the solvent was evaporated under reduced pressure. Water (50 ml) and methanol (10 ml) were added and the pH was adjusted to 2.0 with hydrochloric acid (conc.). The mixture was extracted with ethyl acetate (4×50 ml) and the combined organic fractions were washed with hydrochloric acid (2M, 50 ml) and brine (50 ml) dried (MgSO$_4$) and evaporated under reduced pressure to give 2-[2-methoxy-5-(1H-tetrazol-1-yl) phenyl]-2-oxoethanoic acid as an orange solid (2.11 g, 57%), ¹H NMR (d₆-DMSO) δ 10.10 (1H, s), 8.22 (2H, m), 7.54 (1H, d, J=9.6 Hz), and 3.96 (3H, s).

The aqueous layers were combined, treated with hydrochloric acid (conc., 20 ml) and extracted with ethyl acetate (5×20 ml). The combined organic fractions were dried (MgSO₄) and evaporated under reduced pressure to give additional 2-[2-methoxy-5-(1H-tetrazol-1-yl)phenyl]-2-oxoethanoic acid (1.36 g, 34%).

(ii) Methyl 2-[2-methoxy-5-(1H-tetrazol-1-yl)phenyl]-2-oxoethanoate

Methyl iodide (1.87 ml, 4.26 g, 30 mmol) was added to a mixture of sodium hydrogen carbonate (2.52 g, 30 mmol), and 2-[2-methoxy-5-(1H-tetrazol-1-yl)phenyl]-2-oxoethanoic acid (3.37 g, 13.6 mmol) in dimethylformamide (120 ml) and the mixture was stirred at room temperature for 6 hours. The solvent was evaporated under reduced pressure, saturated aqueous sodium hydrogen carbonate (100 ml) and water (50 ml) were added and mixture was extracted with ethyl acetate (4×100 ml). The combined organic fractions were washed with saturated aqueous sodium hydrogen carbonate (4×100 ml), dried (MgSO₄) and evaporated under reduced pressure to give methyl 2-[2-methoxy-5-(1H-tetrazol-1-yl)phenyl]-2-oxoethanoate as an orange solid (3.36 g, 94%), ¹H NMR (CDCl₃) δ 9.02 (1H, s), 8.11 (1H, d, J=2.8 Hz), 8.03 (1H, dd, J=9.0, 2.8 Hz), 7.23 (1H, d, J=9.0 Hz), 3.99 (3H, s), and 3.96 (3H, s).

(iii) (±)-2,3-cis-Methyl 2-[(1-tert-butoxycarbonyl-2-phenylpiperidin-3-yl)amino]-2-[2-methoxy-5-(1H-tetrazol-1-yl)phenyl]ethanoate Citric acid (1.15 g, 6 mmol) was added to a mixture of (2R3R, 2S3S)-cis-2-phenylpiperidin-3-amine (528 mg, 3 mmol), methyl 2-[2-methoxy-5-(1H-tetrazol-1-yl)phenyl]-2-oxoethanoate (786 mg, 3 mmol) and powdered, activated 3 Å molecular sieves (1.5 g) in methanol (25 ml) and the mixture was stirred at room temperature for 18 hours. Sodium cyanoborohydride (188 mg, 3 mmol) was added and the mixture was stirred at room temperature for 6 hours. Further sodium cyanoborohydride (188 mg, 3 mmol) was added and the mixture was stirred at room temperature for 24 hours. The mixture was filtered through Celite™, washing with methanol and dichloromethane, and the solvent was evaporated under reduced pressure. Ethyl acetate (50 ml) was added and the mixture was extracted with hydrochloric acid (1M, 3×50 ml). The combined aqueous fractions were washed with ethyl acetate (2×50 ml), adjusted to pH 10.0 with saturated aqueous potassium carbonate and extracted with dichloromethane (3×50 ml). The combined organic fractions were dried (MgSO₄) and evaporated under reduced pressure. The residue was dissolved in dichloromethane (5 ml), cooled in ice and di-tert-butyldicarbonate (357 mg, 1.6 mmol) in dichloromethane (5 ml) was added. The mixture was stirred at room temperature for 22 hours, saturated aqueous sodium hydrogen carbonate (20 ml) and water (10 ml) were added and the mixture was extracted with dichloromethane (3×20 ml). The combined organic fractions were dried (MgSO₄) and evaporated under reduced pressure. The residue was purified by flash column chromatography on silica gel, eluting with ethyl acetate/hexane (50:50 increasing to 70:30) to give (±)-2,3-cis-methyl 2-[(1-tert-butoxycarbonyl-2-phenylpiperidin-3-yl)amino]-2-[2-methoxy-5-(1H-tetrazol-1-yl)phenyl]-ethanoate as a colourless foam (415 mg, 26%), ¹H NMR (CDCl₃) δ 8.77 (1H, s), 7.74–6.94 (8H, m), 5.29 (1H, br. s), 4.92 (1H, s), 3.88 (1H, m), 3.81 (3H, s), 3.69 (3H, s), 3.11 (1H, m), 2.80 (2H, m), 1.96–1.53 (4H, m), and 1.39 (9H, s). m/e (CI⁺) 523 (MH⁺).

(iv) (±)-2,3-cis-Methyl 2-[(2-phenylpiperidin-3-yl)amino]-2-[2-methoxy-5-(1H-tetrazol-1-yl)phenyl]ethanoate dihydrochloride Methanolic hydrogen chloride (4M, 4 ml) was added to a stirred, cooled (0° C.) solution of (±)-2,3-cis-methyl 2-[(1-tert-butoxycarbonyl-2-phenylpiperidin-3-yl)amino]-2-[2-methoxy-5-(1H-tetrazol-1-yl)phenyl]ethanoate (339 mg, 0.65 mmol) in methanol (2 ml) and the mixture was stirred at room temperature for 90 minutes. The solvent was evaporated under reduced pressure and the residue was triturated with ethanol (5 ml). The solid was collected and dried in vacuo at 60° C. to give (±)-2,3-cis-methyl 2-[(2-phenylpiperidin-3-yl)amino]-2-[2-methoxy-5-(1H-tetrazol-1-yl)phenyl]ethanoate dihydrochloride as a colourless solid (239 mg, 74%), mp 197–199° C., ¹H NMR (d₆-DMSO) δ 10.07 (1H, s). 9.54 (1H, br. s), 9.12 (1H, br. s), 7.74 (1H, dd, J=8.9, 2.7 Hz), 7.62 (1H, d, J=2.7 Hz), 7.34–7.20 (5H, m), 7.12 (1H, d, J=8.9 Hz), 4.45 (1H, br. s), 4.17 (1H, s), 3.65 (1H, br. s), 3.57 (3H, s), 3.55 (3H, s), 3.32 (2H, m), 3.00 (2H, m), 2.06 (2H, m), 1.85 (1H, m), and 1.65 (1H, m). m/e (CI⁺) 423 (MH⁺).

Analysis: $C_{22}H_{26}N_6O_3 \cdot 2HCl \cdot 0.5H_2O$ requires: C, 52.39; H, 5.79; N, 16.66; Found: C, 52.21; H, 5.70; N, 16.32%. HPLC analysis (210 nm) showed this to consist of an 85:15 mixture of diastereoisomers.

EXAMPLE 3

(±)-2,3-cis-2-[(2-Phenylpiperidin-3-yl)amino]-2-[2-methoxy-5-(1H-tetrazol-1-yl)phenyl]ethanol dihydrochloride (i) (±)-2,3-cis-2-[(1-tert-Butoxycarbonyl-2-phenylpiperidin-3-yl)amino]-2-[2-methoxy-5-(1H-tetrazol-1-yl)phenyl] ethanol Lithium aluminium hydride (0.5M in dimethoxyethane, 3.06 ml, 1.53 mmol) was added dropwise to a stirred, cooled (−40° C.) solution of (±)-2,3-cis-methyl 2-[(1-tert-butoxycarbonyl-2-phenylpiperidin-3-yl)amino]-2-[2-methoxy-5-(1H-tetrazol-1-yl)phenyl]ethanoate (570 mg, 1.09 mmol; from step (iii) of Example 2) in tetrahydrofuran (15 ml) and the mixture was stirred at (−30° C.) for 30 minutes. Methanol (5 ml) was added and the mixture was allowed to warm to room temperature. Saturated aqueous sodium hydrogen carbonate (40 ml) and water (20 ml) were added and mixture was extracted with dichloromethane (3×40 ml). The combined organic fractions were dried (MgSO₄) and evaporated under reduced pressure. The residue was purified by medium pressure liquid chromatography on silica gel, eluting with ethyl acetate/hexane (70:30 increasing to 100:0). The residue was recrystallized from ethyl acetate/hexane (50:50, 15 ml) to give (±)-2,3-cis-2-[(1-tert-butoxycarbonyl-2-phenylpiperidin-3-yl) amino]-2-[2-methoxy-5-(1H-tetrazol-1-yl)phenyl]ethanol as a colourless solid (282 mg, 52%), ¹H NMR (CDCl₃) δ 8.86 (1H, br.s), 7.60 (2H, m), 7.40 (2H, m), 7.22 (3H, m), 6.95 (1H, d, J=8.9 Hz), 5.18 (1H, br.m), 4.35 (1H, br.m), 3.87 (2H, m), 3.81 (3H, s), 3.67 (1H, m), 3.43 (1H, m), 3.00 (1H, m), 2.85 (1H, m), 2.13 (1H, br.s), 1.96 (2H, m), 1.79 (1H, m), 1.60 (1H, m), and 1.32 (9H, s). m/e (CI⁺) 495 (MH⁺).

(ii) (±)-2,3-cis-2-[(2-Phenylpiperidin-3-yl)amino]-2-[2-methoxy-5-(1H-tetrazol-1-yl)phenyl]ethanol dihydrochloride Ethanolic hydrogen chloride (5M, 4 ml) was added to a stirred, cooled (0° C.) suspension of (±)-2,3-cis-2-[(1-tert-butoxycarbonyl-2-phenylpiperidin-3-yl)amino]-2-[2-methoxy-5-(1H-tetrazol-1-yl)phenyl]ethanol (267 mg, 0.54 mmol) in ethanol (2 ml) and the mixture was stirred at room temperature for 90 minutes. The solvent was evaporated under reduced pressure and the residue was triturated with ethanol (5 ml). The solid was collected and dried it vacuo at room temperature to give (±)-2,3-cis-2-[(2-phenylpiperidin-3-yl)amino]-2-[2-methoxy-5-(1H-tetrazol-1-yl)phenyl]ethanol dihydrochloride as a colorless solid (233 mg, 92%), mp 238–240° C., $^1$H NMR (d$_6$-DMSO) δ 10.01 (1H, s), 9.86 (1H, br.s), 7.70 (1H, m), 7.58–7.20 (6H, m), 7.12 (1H, d, J=9.0 Hz), 4.73 (1H, br.s), 4.00–3.06 (10H, m), 3.60 (3H, s), 2.29 (2H, m), 1.94 (1H, m), and 1.78 (1H, m). m/e (CI$^+$) 395 (MH$^+$).

HPLC analysis (210 nm) showed this to consist of a 93:7 mixture of diastereoisomers.

What is claimed is:

1. A compound of formula (I):

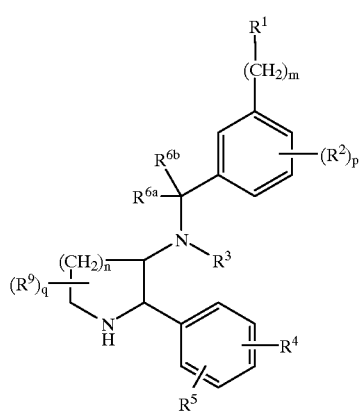

(I)

wherein

R$^1$ represents a 5- or 6-membered aromatic heterocyclic group containing 1, 2, 3 or 4 heteroatoms selected from nitrogen, oxygen and sulphur, which is optionally substituted by one or two substituents, selected from C$_{1-4}$alkyl, C$_{3-7}$cycloalkyl, C$_{3-7}$cycloalkylC$_{1-4}$alkyl, SR$^x$, SOR$^x$, SO$_2$R$^x$, phenyl, NR$^a$R$^b$, NR$^a$COR$^x$, CH$_2$COCF$_3$ and CF$_3$, where R$^a$ and R$^b$ are independently hydrogen or C$_{1-4}$alkyl and R$^x$ is C$_{1-4}$alkyl;

R$^2$ represents halogen, C$_{1-6}$alkyl, C$_{1-6}$alkoxy, CF$_3$, OCF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;

R$^3$ represents hydrogen or C$_{1-6}$alkyl;

R$^4$ represents hydrogen, halogen, C$_{1-6}$alkyl, C$_{1-6}$alkoxy, hydroxy, CF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;

R$^5$ represents hydrogen, halogen, C$_{1-6}$alkyl, C$_{1-6}$alkoxy substituted by C$_{1-4}$alkoxy or CF$_3$;

R$^{6a}$ represents hydrogen, methyl or ethyl;

R$^{6b}$ represents C$_{1-6}$alkyl substituted by a hydroxy group;

R$^9$ represents halogen, C$_{1-6}$alkyl, oxo, CO$_2$R$^a$ or CONR$^a$R$^b$;

m is zero or 1;

n is 2;

p is zero, 1 or 2; and q is zero, 1 or 2;

or a pharmaceutically acceptable salt or prodrug thereof.

2. A compound as claimed in claim 1 wherein R$^1$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each of which heteroaryl groups being optionally substituted as defined in claim 1.

3. A compound as claimed in claim 1 wherein R$^1$ is a 5-membered aromatic heterocyclic group selected from:

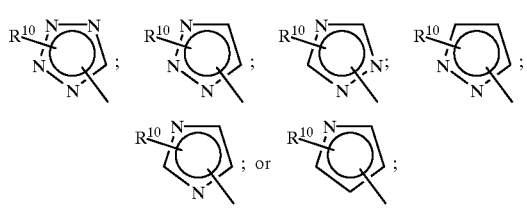

where R$^{10}$ is hydrogen, C$_{1-4}$alkyl, C$_{3-7}$cycloalkyl, C$_{3-7}$cycloalkylC$_{1-4}$alkyl, SR$^x$, SOR$^x$, SO$_2$R$^x$, phenyl, NR$^a$R$^b$, NR$^a$COR$^x$, CH$_2$COCF$_3$ or CF$_3$, where R$^a$ and R$^b$ are independently hydrogen or C$_{1-4}$alkyl, and R$^x$ is C$_{1-4}$alkyl.

4. A compound as claimed in claim 3 wherein R$^1$ is the group

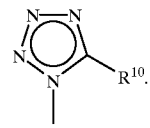

wherein R$^{10}$ is as defined in claim 3.

5. A compound as claimed in any claim 1 wherein R$^2$ is C$_{1-4}$alkyl, C$_{1-4}$alkoxy, halogen, CF$_3$ or OCF$_3$.

6. A compound as claimed in claim 1 wherein R$^2$ is in the meta- or para-position with respect to the group R$^1$-(CH$_2$)$_m$—.

7. A compound as claimed in claim 1 wherein R$^3$ is hydrogen or C$_{1-4}$alkyl.

8. A compound as claimed in claim 1 wherein R$^4$ is hydrogen and R$^5$ is hydrogen or 4-fluoro.

9. A compound of formula (Ia):

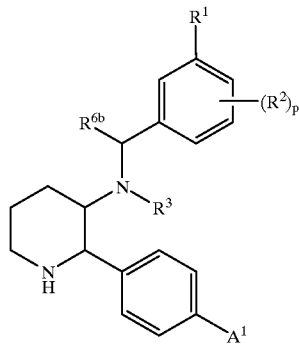

(Ia)

wherein
$R^1$, $R^2$, $R^3$, $R^{6b}$ and p are as defined in claim 1; and
$A^1$ is fluorine or hydrogen;
or a pharmaceutically acceptable salt or prodrug thereof.

10. A compound selected from:
(±)-2,3-cis-N-{1-[2-methoxy-5-(1H-tetrazol-1-yl)phenyl]ethyl}-2-phenylpiperidin-3-amine;
(±)-2,3-cis-2-[(2-phenylpiperidin-3-yl)amino]-2-[2-methoxy-5-(1H-tetrazol-1-yl)phenyl]ethanol;
or a pharmaceutically acceptable salt or prodrug thereof.

11. A pharmaceutical composition comprising a compound as claimed in claim 1 in association with a pharmaceutically acceptable carrier or excipient.

12. A method for the treatment of a physiological disorder having an excess of tachykinins, which method comprises administration to a patient in need thereof of a tachykinin reducing amount of a compound according to claim 1.

13. A method according to claim 12 for the treatment of pain or inflammation.

14. A method according to claim 12 for the treatment of migraine.

15. A method according to claim 12 for the treatment of emesis.

16. A method according to claim 12 for the treatment of postherpetic neuralgia.

17. A process for the preparation of a compound as claimed in claim 1 which comprises:

(A) reacting a compound of formula (II) with a compound of formula (III):

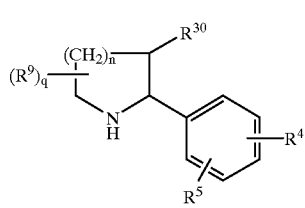

(II)

-continued

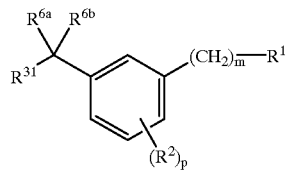

(III)

wherein $R^1$, $R^2$, $R^4$, $R^5$, $R^{6a}$, $R^{6b}$, $R^9$ m, n, p and q are as defined in claim 1, except that any reactive moiety is protected by a suitable protecting group; and one of $R^{30}$ and $R^{31}$ represents a leaving group and the other of $R^{30}$ and $R^{31}$ represents $NHR^3$, where $R^3$ is as defined in claim 1; in the presence of a base, followed by deprotection, if required; or (B), where $R^{6a}$ is hydrogen, reductive amination of a compound of formula (II) in which $R^{30}$ is the group $NHR^3$, with a compound of formula (IV):

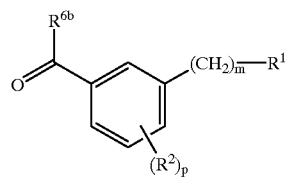

(IV)

in the presence of a reducing agent; or (C), where m is zero and $R^1$ is a tetrazol-1-yl group substituted by a 5-amino moiety, reaction of intermediates of formula (V):

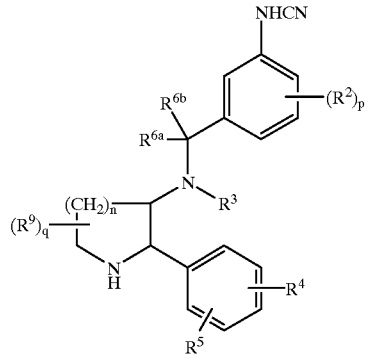

(V)

with ammonium chloride and sodium azide at elevated temperature; or (D), a coupling reaction between a compound of formula (VI) and (VII):

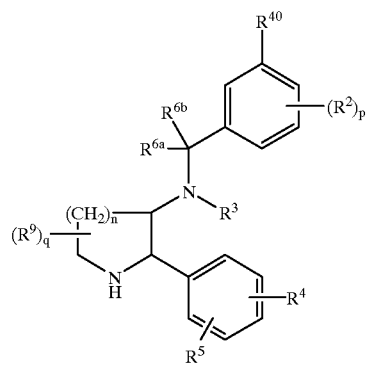
(VI)

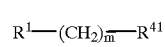
(VII)

wherein one of $R^{40}$ and $R^{41}$ is $B(OH)_2$ or $Sn(alkyl)_3$ or a derivative thereof, and the other is a leaving group; or (E), reduction of a compound of formula (VIII):

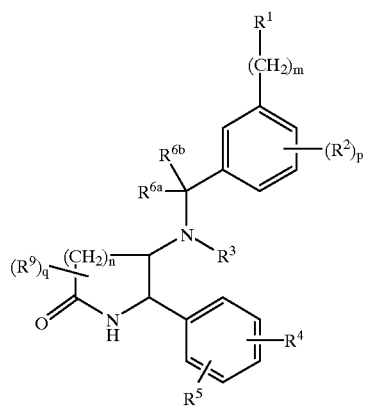
(VIII)

with the proviso that $R^9$ is not oxo;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt or prodrug thereof.

* * * * *